United States Patent [19]

Warman

[11] 4,411,378
[45] Oct. 25, 1983

[54] DISPOSABLE SURGICAL STAPLING INSTRUMENT HAVING AN ANVIL WITH COEXTENSIVE LATERAL FLANGES

[75] Inventor: Thomas E. Warman, Williamsburg, Ohio

[73] Assignee: Senco Products, Inc., Cincinnati, Ohio

[21] Appl. No.: 229,080

[22] Filed: Jan. 28, 1981

[51] Int. Cl.³ .............................................. B25C 5/02
[52] U.S. Cl. ................................ 227/19; 128/334 R; 227/DIG. 1
[58] Field of Search .................. 227/1 B, 19, DIG. 1; 128/334, 335

[56] References Cited

U.S. PATENT DOCUMENTS

| | | | |
|---|---|---|---|
| 3,873,016 | 3/1975 | Fishbein | 227/19 |
| 3,889,338 | 6/1975 | Hosaka | 227/DIG. 1 B |
| 4,109,844 | 8/1978 | Becht | 227/19 X |
| 4,179,057 | 12/1979 | Becht | 227/19 |
| 4,187,970 | 2/1980 | Furutu | 227/67 X |

*Primary Examiner*—Fred Silverberg
*Assistant Examiner*—Timothy V. Eley
*Attorney, Agent, or Firm*—Frost & Jacobs

[57] ABSTRACT

A disposable surgical stapling instrument is taught for forming and implanting surgical staples in the skin or fascia of a patient. The instrument comprises a body made up of two mating halves and having a rear handle portion, a forward portion and a staple magazine portion beneath the forward portion. The forward portion of the body houses a staple driver shiftable therein between a first retracted position and a second extended staple forming and implanting position. A trigger is pivotally mounted within the body and is directly connected to the staple driver to shift the driver between its first and second positions. A portion of the trigger is exposed beneath the body handle portion for actuation by the surgeon. A leaf spring is located within the body above the trigger to urge the trigger to its unactuated position and the staple driver to its first position. The magazine portion houses an anvil plate terminating at its forward end in a coextensive anvil surface located beneath the staple driver. The anvil plate is configured to support the legs of all but the forwardmost staple of a row thereof mounted thereon. The magazine portion also houses a feeder assembly for the row of staples.

3 Claims, 16 Drawing Figures

DISPOSABLE SURGICAL STAPLING INSTRUMENT HAVING AN ANVIL WITH COEXTENSIVE LATERAL FLANGES

CROSS REFERENCE TO RELATED APPLICATION

The surgical stapling instrument of the present invention constitutes an improvement of that surgical stapling instrument taught in U.S. Pat. No. 4,179,057, issued Dec. 18, 1979 in the names of Carl T. Becht and J. Charles Hueil and entitled DISPOSABLE SURGICAL STAPLING INSTRUMENT.

TECHNICAL FIELD

The invention relates to a surgical stapling instrument, and more particularly to such an instrument of improved and simplified construction and having an improved anvil plate.

BACKGROUND ART

The stapling instrument of the present invention can be used in any situation where the element to be stapled is approached from one side only and the staple is formed about an anvil, rather than against an anvil. The stapling instrument is particularly adapted for use as a surgical stapling instrument and will, for purposes of an exemplary showing, be so described. By proper selection of materials, the instrument may be manufactured as a reusable instrument. It construction is such, however, that the majority of its parts lend themselves well to be molded of plastic and the instrument can readily be produced as a single-use disposable instrument. For purposes of an exemplary showing, the instrument will be described in its application as a single-use, disposable surgical stapling instrument.

Surgeons have come more and more to the use of staples, rather than conventional thread sutures, for closing wounds or incisions in the skin and fascia of a patient. This is true primarily because the use of staples is a far easier procedure and, of even greater importance, is very much faster. The use of staples substantially reduces the time required for suturing and thus the length of time the patient must be maintained under anesthesia.

Prior art workers have developed various types of surgical stapling instruments, examples of which are taught in U.S. Pat. Nos. 3,618,842; 3,643,851; 3,717,294; 3,837,555 and 3,873,016. In general, the prior art instruments are complex in construction and expensive to manufacture. They do not lend themselves to a disposable construction. Prior art surgical staplers generally require a magazine or cartridge for the staples and a portion of the force required to actuate these instruments is expended in shifting a staple to an anvil means, prior to the formation of the staple about the anvil means. As a result, some prior art surgical staples require upwards of 20 pounds force to form and implant a surgical staple.

An important advance was made in the surgical stapling instrument art by U.S. Pat. Nos. 4,109,844 and 4,179,057. These references teach single-use, disposable instruments provided with an anvil plate by which the surgical staples are supported and along which they are fed. The anvil plate terminates in a coextensive anvil surface and means are provided, separate from the staple forming and implanting means, to constantly urge and advance the row of staples along the anvil plate to place a forwardmost staple of the row on the anvil surface to be formed by a staple driver. All of the force required to operate these surgical stapling instruments is directed to the forming and implanting of the forwardmost surgical staple and no part of the force exerted by the surgeon is required to shift a staple from a cartridge or magazine to the anvil surface about which it is formed.

The present invention provides a disposable surgical stapling instrument which represents an improvement over that of the above mentioned U.S. Pat. No. 4,179,057. The surgical stapling instrument of the present invention is characterized by all of the advantages of the surgical stapler taught in the above mentioned U.S. Pat. No. 4,179,057. In addition, the surgical stapling instrument of the present invention is characterized by an unique overall construction which is even simpler and requires fewer parts; a unique trigger and trigger-biasing means, an improved surgical staple magazine constituting an integral, one-piece part of the surgical stapling instrument body; and an improved anvil plate which narrows the opening through which the forwardmost surgical staple is formed. This latter advance accomplishes two things. First, the anvil plate fully supports the leg and crown portions of that staple adjacent the forwardmost staple of the row, as well as all of the staples therebehind. This assures that that staple immediately behind the forwardmost one of the row will be in proper position for forming when it becomes the forwardmost staple of the row. Secondly, with this second staple being fully suported, gives better support to the forwardmost staple of the row being formed, since it helps hold the forwardmost staple under the former and reduces possible leg roll during the forming procedure.

DISCLOSURE OF THE INVENTION

According to the invention there is provided a disposable surgical stapling instrument for forming and implanting surgical staples in the skin or fascia of a patient. The surgical stapling instrument comprises a body made up of two mating halves and having a rearward handle portion, a forward portion and a staple magazine portion located beneath the forward portion.

A staple driver is slidably mounted in the forward portion of the instrument body. The staple driver is shiftable between a first retracted or normal position and a second extended or staple forming and implanting position.

A trigger is pivotally mounted within the body and a portion of the trigger is exposed beneath the body handle portion for actuation by the surgeon. The forward end of the trigger has a nose portion thereon in direct engagement with the staple driver. The arrangement is such that when the exposed portion of the trigger is squeezed and cause to pivot into the handle portion of the body, the nose portion of the trigger shifts the staple driver from its first retracted position to its second extended position. A leaf spring is located within the body (primarily in the handle portion thereof) above the trigger to urge the trigger to its normal unactuated position and the staple driver to its normal or first retracted position.

The magazine portion of the body houses an anvil plate, the anvil plate terminating at its forward end in a coextensive anvil surface located beneath the staple driver. A row of surgical staples is mounted on the anvil plate and is slidable therealong. The anvil plate is configured to support the legs of all but the forwardmost staple of the row thereof.

The magazine portion of the instrument body also houses a surgical staple feeder assembly. The feeder assembly comprises a feeder shoe slidably mounted on the anvil plate behind the row of surgical staples and a simple coil spring which constantly urges the feeder shoes against the row of staples and constantly urges the row of staples along the anvil plate to place a forwardmost staple of the row on the anvil surface thereof to be formed by the staple driver.

BRIEF DESCRIPTION OF THE DRAWINGS

FIG. 6 is an elevational view of the right body half, similar to FIG. 4, and illustrating the staple driver, the trigger, the leaf spring, the anvil plate, a row of surgical staples and the staple feeder assembly mounted therein.

DETAILED DESCRIPTION OF THE INVENTION

Figure 1:
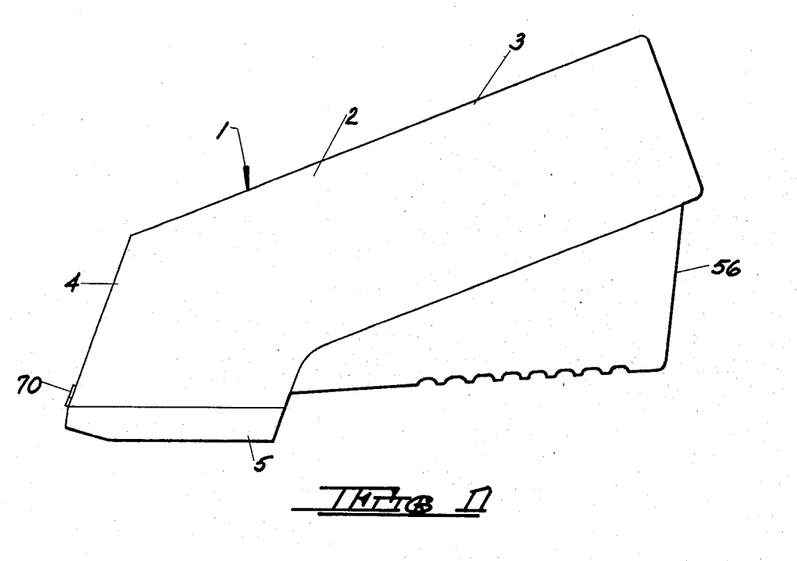
FIG. 1 is a side elevational view of the surgical stapling instrument of the present invention.
Figure 2:
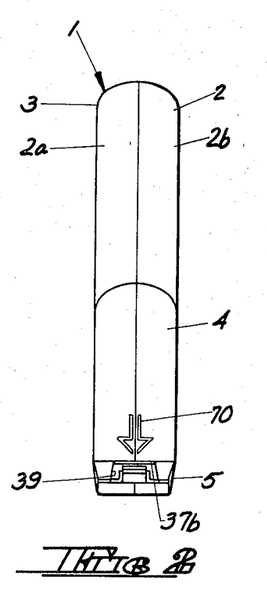
FIG. 2 is a front elevational view of the surgical stapling instrument of FIG. 1.
Figure 3:
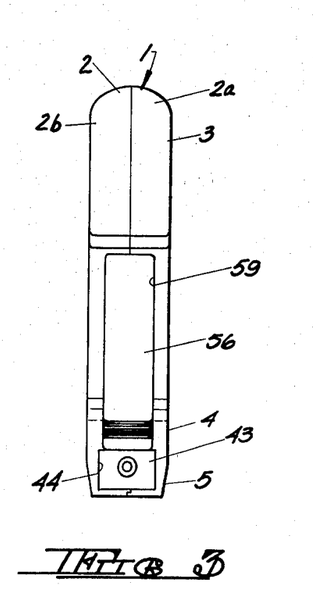
FIG. 3 is a rear elevational view of the surgical stapling instrument of FIG. 1.

In all of the figures, like parts have been given like index numerals. Reference is first made to FIGS. 1 through 3 wherein the surgical stapling instrument is generally indicated at 1. The surgical stapling instrument comprises a body 2 made up of a right body half 2a and a left body half 2b, the body halves capable of being assembled in mated relationship, as shown in FIGS. 1 through 3. The body 2 has a rearward portion 3 constituting a handle portion. It also has a forward portion 4 and a magazine portion 5 located immediately below the forward portion 4. It will be noted that the rearward or handle portion 3 of body 3 is angularly related to the forward portion 4 so that the instrument can be readily grasped by the hand of the surgeon and held in its normal position of use as illustrated in FIGS. 1 through 3. It will be understood by one skilled in the art that once so held in the surgeon's hand, the instrument can be oriented in any direction, depending upon the patient position and the area of the patient being sutured.

Figure 4:
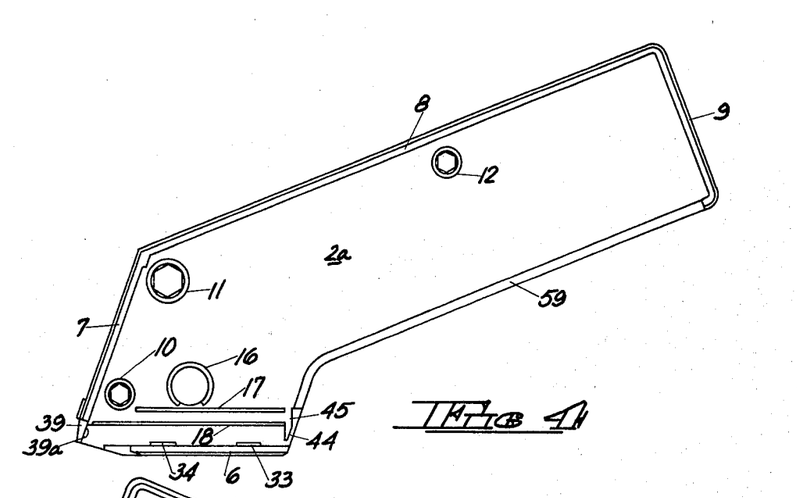
FIG. 4 is a side elevational view of the right body half of the surgical stapling instrument of the present invention, illustrating the interior thereof.
Figures 5, 7:
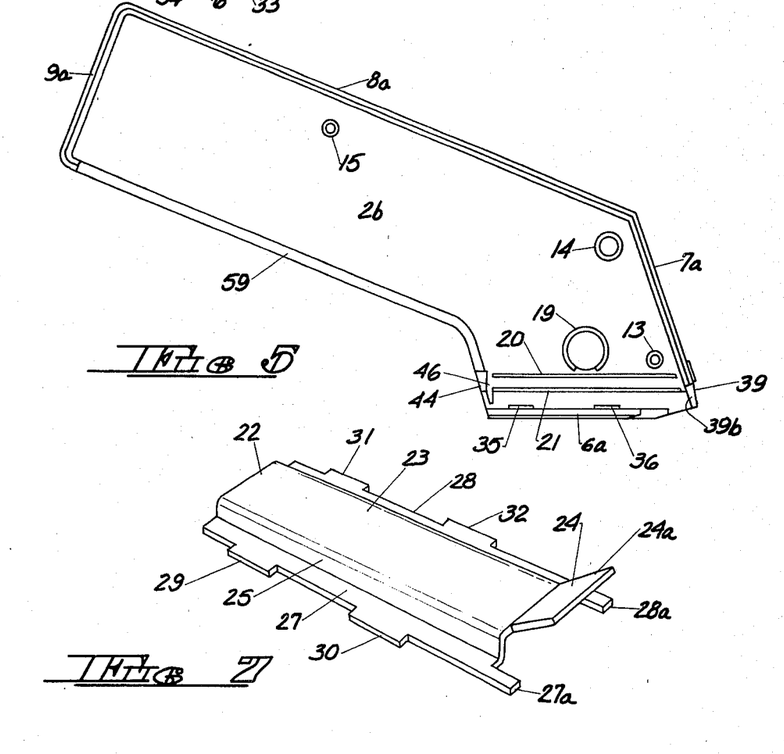
FIG. 5 is an elevational view of the left body half of the surgical stapling instrument of the present invention, illustrating the interior thereof.
FIG. 7 is a perspective view of the anvil plate of the present invention.

The right body half 2a and the left body half 2b are illustrated in FIGS. 4 and 5, respectively. The right body half 2a has edge portions 6 through 9 adapted to engage and be joined to edge portions 6a through 9a, respectively, of left body half 2b. As can be seen from FIGS. 4, 5 and 10, the edges 6 through 9 and the edges 6a through 9a are oppositely stepped so as to have a mating relationship when abutted. Right body half 2a has three annular elements 10, 11 and 12 formed thereon, the annular elements 10, 11 and 12 constitute three female sockets. The left body half 2b has three upstanding hollow male members 13, 14 and 15 thereon. When the body halves 2a and 2b are joined together, male members 13, 14 and 15 are received within female sockets 10, 11 and 12, respectively, with a frictional fit.

The body halves 2a and 2b in the embodiment illustrated are molded of appropriate plastic material suitable for use in a surgical environment and capable of withstanding sterilization by any one or more of the standard sterilization procedures well known in the art. Once the internal components of the surgical stapling instrument (to be described hereinafter) have been assembled in one of the body halves, the body halves are joined together. In addition to the frictional engagement of male members 13 through 15 in female sockets 10 through 12, the mated edges 6 through 9 and 6a through 9a may be permanently bonded by gluing, welding or the like. It will be understood by one skilled in the art that if the instrument of the present invention is to be non-disposable and reuseable, body halves 2a and 2b can be fabricated of stainless steel or other appropriate material suitable for use in a surgical environment and capable of being sterilized. Under such circumstances, the body halves will be held together by removable fastening means such as screws or the like, to enable disassembly of the instrument for purposes of cleaning and sterilization.

Body half 2a has an annular flange 16 and a pair of rectilinear flanges 17 and 18 in parallel spaced relationship. The body half 2b has an annular flange 19, equivalent to annular flange 16, and a pair of rectilinear flanges 20 and 21, equivalent to flanges 17 and 18, respectively. When the body halves are assembled, annular flanges 16 and 19 are opposed and coaxial and flanges 17 and 18 are in opposed parallel spaced relationship to flanges 20 and 21, respectively.

Reference is now made to FIG. 6. FIG. 6 illustrates the right body half 2a of the surgical stapling instrument with the internal elements mounted therein. Turning first to the magazine portion 5 of the surgical stapling instrument, there is housed therein an anvil plate 22. The anvil plate 22 is best seen in FIG. 7. The anvil plate 22 is preferably formed of an appropriate metal for use in a surgical environment, such as stainless steel or the like. The anvil plate 22 has a longitudinally extending raised central portion 23. At its forwardmost end, the raised central portion 23 has an extension 24 comprising an integral one-piece part of the raised portion 23 and lying at a slight angle thereto. The extension 24 constitutes an anvil and the upper surface 24a of extension 24 constitutes an anvil surface which is coextensive with the upper surface of the raised central portion 23.

Figure 10:
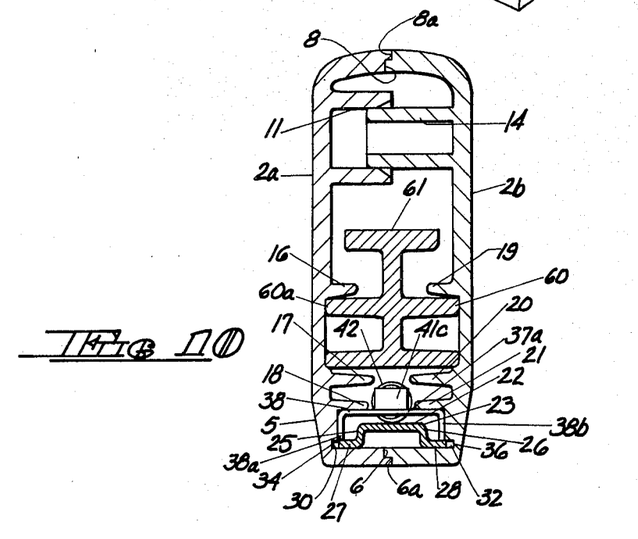
FIG. 10 is a cross sectional view taken along section line 10—10 of FIG. 6.
Figure 11:
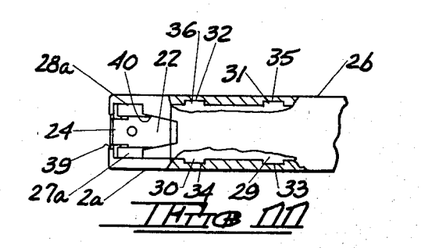
FIG. 11 is a fragmentary bottom view of the surgical stapling instrument.

The raised central portion 23 of anvil plate 22 has lateral edges which terminate in downwardly depending portions 25 and 26 (see also FIG. 10). The downwardly depending portions 25 and 26, in turn, terminate in laterally extending flanges 27 and 28. Flange 27 is provided with a pair of extensions 29 and 30. Similarly, flange 28 is provided with a pair of extensions 31 and 32. The right body half 2a (see FIG. 4) has a pair of recesses 33 and 34 formed therein. In similar fashion, the left body half 2b (FIG. 5) has a pair of recesses 35 and 36 formed therein. When the body halves 2a and 2b are joined together with the anvil plate 22 properly located therebetween, the extensions 29 and 30 of flange 27 will be received within recesses 33 and 34 of body half 2a, respectively. Similarly, the extensions 31 and 32 of flange 28 will be received within recesses 35 and 36 of body half 2b. In this way the anvil plate 22 is properly located and locked within the body halves. This is illustrated in FIGS. 10 and 11. It is also evident from FIG. 10 that anvil plate flanges 27 and 28 rest upon the bottom portions of body halves 2a and 2b.

The anvil plate 22, including the raised central portion 23, the downwardly depending portions 25 and 26 and the laterally extending flanges 27 and 28 are so configured that the portions 23, 25 and 26 are straddled by a row of staples 37, in face-to-face relationship. This is clearly shown in FIG. 10 which illustrates one of the staples 37a of the row 37. The staple 37a has a crown portion 38 and a pair of downwardly depending legs 38a and 38b terminating in pointed tips. The tips of the legs 38a and 39b ride along and are supported by flanges 27 and 28.

As is evident from FIG. 10, the inside wall surfaces of magazine portion 5, together with flanges 18 and 21, form a magazine for the row 37 of surgical staples, in cooperation with anvil plate 22. As is evident from FIG. 2, the forwardmost surface of magazine portion 5 has a notch 39 formed therein. The notch is so dimensioned that an unformed staple cannot pass therethrough. As a result, the forwardmost staple 37b of the row 37 will abut the inside surfaces 39a and 39b of the magazine portion adjacent the notch 39 (see FIGS. 4 and 5). Only when the forwardmost staple 37b of row 37 is fully formed and implanted, will it be of proper dimensions to pass through the notch 39, as will be described hereinafter. As can clearly be seen in FIG. 11, the bottom surface of magazine portion 5 has a notch 40 formed therein, in part coextensive with notch 39. The notch 40 exposes the forward end of anvil plate 22, enabling the forwardmost staple of the row 37 to be formed and implanted in the skin of the patient.

It will be noted from FIGS. 7 and 11 that flanges 27 and 28 of anvil plate 22 have forward extensions 27a and 28a, assuring that the legs of all of the surgical staples of the row 37 thereof are supported (as shown in FIG. 10) save the forwardmost staple 37b of the row. As can most clearly be seen in FIGS. 6 and 11, the extensions 27a and 28a narrow the gap through which the forwardmost staple 37b is formed and implanted.

Figure 8:
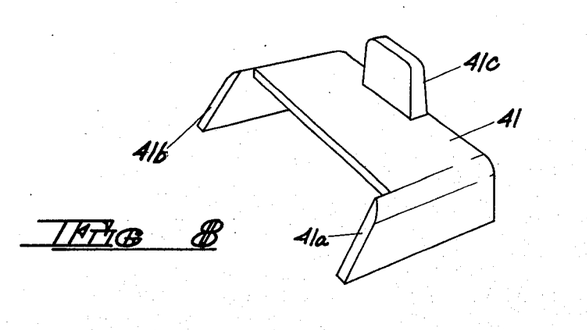
FIG. 8 is a perspective view of the feeder shoe of the present invention.

The magazine portion 5 of the surgical stapling instrument also contains a feeder assembly for the row 37 of surgical staples. Turning again to FIG. 6, the feeder assembly comprises a feeder shoe 41, a coil spring 42 and a plug 43. Feeder shoe 41 is illustrated in FIG. 8. The feeder shoe 41 constitutes a generally inverted U-shaped member having overall dimensions approximating those of the surgical staples themselves. The feeder shoe is adapted to straddle anvil plate 22 behind the row 37 of surgical staples. The downwardly depending portions of feeder shoe 41 have forward faces 41a and 41b which slope upwardly and rearwardly at approximately the same angle as the inside surfaces 39a and 39b of magazine portion 5 (see FIGS. 4 and 5). The feeder shoe 41 also has a centrally located upstanding lug 41c, the purpose of which will be evident hereinafter.

Figure 9:
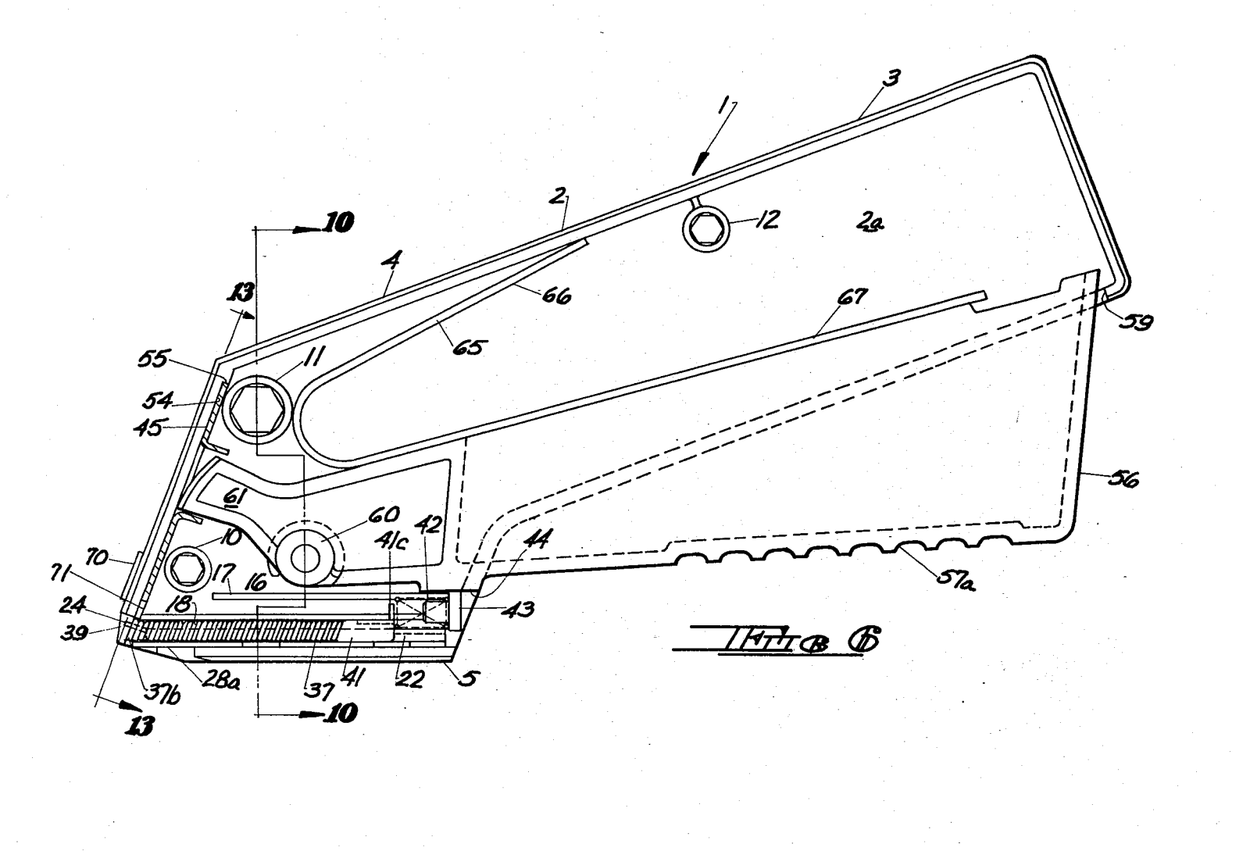
FIG. 9 is a perspective view of the magazine plug.

As can be seen in FIGS. 3 through 6, the rearward end of magazine portion 5 has a rectangular opening 44. This rectangular opening permits the loading of the surgical staples within the magazine portion, together with feeder shoe 41. The opening 44, once the loading procedure has been completed, is closed by plug 43. The plug 43 has a pair of laterally extending flanges 43a and 43b adapted to engage the notch 45 in right body half 2a (see FIG. 4) and the notch 46 in left body half 2b (see FIG. 5). The flanges 43a and 43b slope forwardly and inwardly, as shown in FIG. 9, so that plug 43 can be inserted in opening 44 with a snap fit. The plug 43 has a hollow cylindrical extension 43c at its forward end. As will be evident from FIG. 6, the extension 43c serves as a mount for the rearward end of coil spring 42. The forward end of coil spring 42 engages the upstanding flange 41c of feeder shoe 41. Spring 42 will therefore urge feeder shoe 41 forwardly. Feeder shoe 41, in turn, will assure that the forwardmost staple of the row (throughout the row as the row is depleted) will always be in abutment with the inside magazine surfaces 39a and 39b (FIGS. 4 and 5). Flange pairs 17-20 and 18-21 serve as guide means for spring 42 assuring its proper alignment (FIG. 10).

Figure 12:
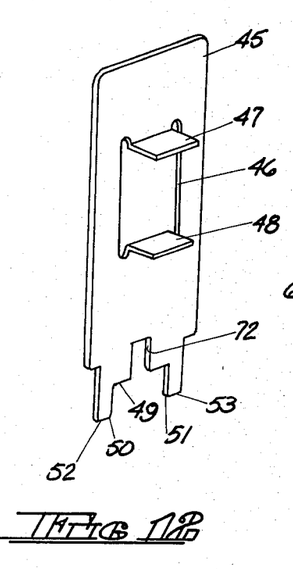
FIG. 12 is a perspective view of the surgical staple driver of the present invention.
Figure 13:
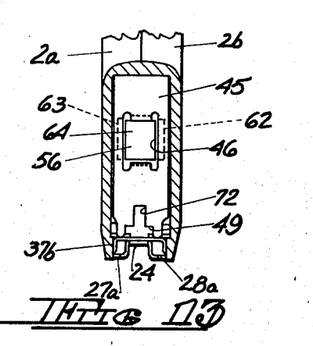
FIG. 13 is a fragmentary cross sectional view taken along section line 13—13 of FIG. 6.

Reference is now made to FIGS 6, 12 and 13. Mounted within the forward portion 4 of the surgical stapling instrument body 2 there is a staple driver 45. As can be most clearly seen in FIG. 12, the staple driver 45 comprises a substantially planar, substantially rectangular element preferably made of metal suitable for use in a surgical environment, such as stainless steel or the like. The staple driver 45 is provided with a central opening 46 from which rearwardly extending tabs 47 and 48 are formed. The purpose of tabs 47 and 48 will be described hereinafter.

At its lowermost end the staple driver has a staple forming notch 49 formed therein. At the lowermost corners 50 and 51 of the notch, the staple driver 45 may be slightly rounded, as shown in FIG. 12. This assists in bending the crown portions of the staples, as will be described hereinafter. The lowermost edges 52 and 53 and the adjacent rounded corners 50 and 51 (the first portions of the staple driver to contact the crown of a staple) may be slightly grooved to assure that the staple being formed by the driver is properly aligned during the initial phase of the staple forming procedure.

As is most clearly shown in FIG. 6, the staple driver 45 is located in abutment with the front inside surface 54 of the forward portion 4 of the instrument. The staple driver 45 is slidable along inside surface 54 between a first retracted or normal position illustrated in FIGS. 6, 13 and 15, and a second extended or staple forming and implanting position shown in FIG. 16. The inside surface 54 of forward portion 4 of the instrument is stepped as at 55 to serve as a stop for the staple driver 45 to determine its first retracted or normal position.

Figure 14:
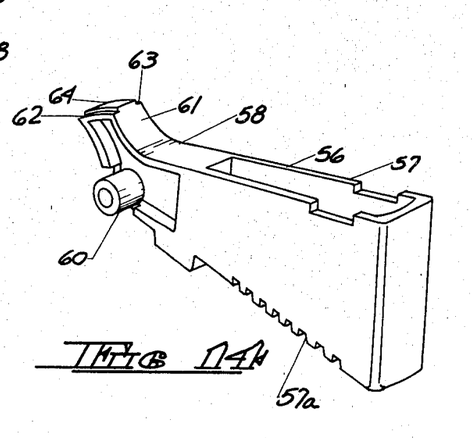
FIG. 14 is a perspective view of the trigger of the present invention.

The means to shift the staple driver between its first and second positions is illustrated in FIGS. 6 and 14. This means comprises a trigger 56. The trigger 56 (best shown in FIG. 14) lends itself well to be molded of an appropriate plastic material for use in a surgical environment and comprises a rearward portion 57 and a forward portion 58. The rearward portion 57 is hollow, as shown, and extends through an elongated opening 59 (see FIGS. 4 through 6) in the rearward or handle portion 3 of the instrument body 2. The lower edge portion of trigger 56 is adapted to be grasped by the fingers of the surgeon and, to this end, may be notched or serrated as at 57a. The forward portion 58 of trigger 56 is provided with a pair of diametrically opposed, laterally extending, integral pivot pins, 60 and 60a (see FIGS. 10 and 14). Pivot pin 60 is adapted to be rotatably received in annular flange 19 of left body half 2b. The other pivot 60a is similarly adapted to be rotatively received in annular flange 16 of right body half 2a.

The forward portion 58 of trigger 56 terminates in a nose 61. Nose 61, itself, terminates in arcuate surfaces 62 and 63, flanking a raised central arcuate surface 64. As will be evident from FIGS. 6, 12 and 14, the forward end of nose 61 is adapted to be received between the rearwardly extending tabs 47 and 48 of staple driver 45. The central raised arcuate surface 64 is of such width as to extend into perforation 46 of the staple driver and the arcuate surfaces 62 and 63 bear against those portions of staple driver 45 to either side of perforation 46. Thus, the nose portion 61 of trigger 56 maintains the staple driver in abutment with the interior surface 54 of the forward portion 4 of the instrument.

As is most clearly shown in FIG. 6, a leaf spring 65 is mounted in the body 2 of instrument 1. The leaf spring is substantially U-shaped, having a first leg 66 bearing against the upper inside surface of instrument body 2 and a second leg 67 lying along the upper surface of trigger 56. It will be evident from FIG. 6 that spring 65 will maintain trigger 56 in its normal position as illustrated in that Figure. This, in turn, assures that staple driver 45 is in its first retracted or normal position. Upon squeezing trigger 56 to cause it to pivot in a counterclockwise position (as viewed in FIG. 6), the nose portion 61 thereof will cause staple driver 45 to shift to its second extended or staple driving and implanting position.

Figure 15:
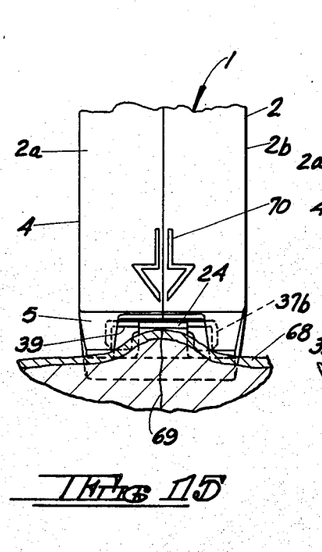
FIG. 15 is a fragmentary front elevational view of the surgical stapling instrument of the present invention illustrating its placement over an incision to be sutured.
Figure 16:
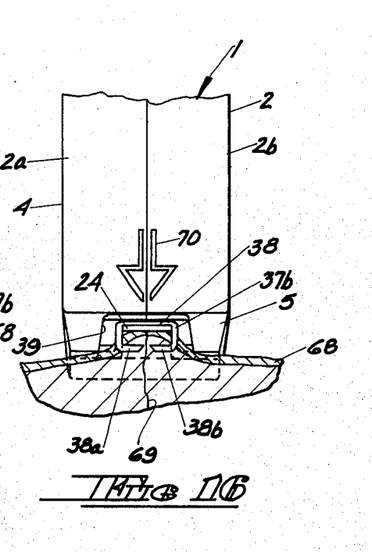
FIG. 16 is a fragmentary front elevational view, similar to FIG. 15, and illustrating the forwardmost surgical staple formed and implanted in the skin of the patient.

The elements of the surgical stapling instrument 1 having been described in detail, its operation can be set forth as follows. The surgical stapling instrument of the present invention comes to the surgeon in assembled, loaded and sterilized form. Grasping the instrument in his right or left hand by rearward handle portion 3 and with his fingers about trigger 56, the surgeon locates the instrument over the wound or incision to be sutured. This is illustrated in FIG. 15 wherein a patient's skin is shown at 68 containing a wound or incision 69. The forwardmost exterior surface of the instrument 1 may, if desired, be provided with indicia 70 to assist the surgeon in centering the surgical stapling instrument 1 over incision 69. The indicia 70 in the exemplary embodiment of the present invention is shown as being a raised element on each of the body halves 2a and 2b which, when the body halves are joined together defines an arrow. When placed upon the incision as shown in FIG. 15, the notch 39 in the forward end of magazine portion 5 and the notch 40 in the forward bottom part of magazine portion 5 will cause the patient's skin 68 to bulge slightly toward anvil 24.

Once the instrument 1 is properly located over incision 69, the surgeon squeezes trigger 56 against the action of spring 65. As indicated heretofore, pivoting of trigger 56 in a counterclockwise direction (as viewed in FIG. 6) will cause the nose portion 61 of trigger 56 to shift staple driver 45 to its second extended or staple forming and implanting position. As the staple driver shifts downwardly, its lowermost edges 52 and 53 will contact the crown of forwardmost staple 37b to either side of anvil 24. As the driver 45 moves further downwardly, the curved portions 50 and 51 thereof will initiate bending of the crown portion 38 of the forwardmost staple 37b. This, in turn, will cause staple legs 38a and 38b to enter and be implanted in the skin 68. At the completion of the forming and implanting procedure, the staple will have the configuration shown in FIG. 16, closing incision 69. In this configuration, the fully formed and implanted staple 37b is now of such dimension that it can pass through notch 39 in the forwardmost end of the magazine portion 5, slipping off of anvil 24 under the urging of spring 42. Upon release of trigger 56, spring 65 will return the trigger to its normal position as shown in FIG. 6. This, in turn, will cause staple former 45 to return to its first retracted or normal position. In the meantime, coil spring 42 and feeder shoe 41 will advance the next forwardmost staple of row 37 onto anvil surface 24a and in abutment with the interior wall surfaces 39a and 39b of the forward end of magazine portion 5. Since the anvil plate flange extensions 27a and 28a support that staple adjacent the forwardmost staple of the row and effectively narrow the gap through which the forwardmost staple is formed and implanted, the forwardmost staple will be stabilized by that staple immediately behind it reducing or eliminating the possibility of leg roll during formation of the forwardmost staple. In addition, the staple just behind the forwardmost staple will be in proper position to become the forwardmost staple after the next forming and implanting procedure.

It is within the scope of the present invention to form a lug half on each of body halves 2a and 2b on the inside forward surface thereof. Such a lug half is shown at 71 in FIG. 6. When the body halves 2a and 2b are joined together, lug half 71 on body half 2a will lie adjacent an identical lug half on body portion 2b, forming a rectangular lug located just above the crown of the forwardmost staple 37b. This lug will limit the amount of bowing of the staple crown during the forming and implanting procedure. When such lug halves are provided on body halves 2a and 2b, staple driver 45 will have an additional notch 72 formed therein (see FIG. 12) to provide clearance for the lug.

Modifications may be made in the invention without departing from the spirit of it. For example, leaf spring 65 can be replaced by a compression spring or any other appropriate type of biasing means.

What is claimed is:

1. A surgical stapling instrument for forming and implanting surgical staples in the skin or fascia of a patient, said instrument comprising an elongated body made up of two mating halves forming a rearward handle portion, a forward portion and a surgical staple magazine portion located beneath said forward portion, an anvil plate mounted within said magazine portion, said anvil plate having forward and rearward ends and comprising an elongated member of inverted U-shaped cross section having a longitudinally extending raised planar central portion, said raised central portion having longitudinal edges terminating in coextensive downwardly depending portions, each of said downwardly depending portions terminating in a coextensive flange portion extending laterally of said downwardly depending portion and said central portion, a coextensive extension on said central portion at said forward end of said anvil plate lying at a slight upward angle to said central portion, said extension having an upper surface comprising an anvil surface, a row of surgical staples slidably mounted on said anvil plate, a feeder assembly mounted in said magazine portion to constantly urge and advance said row of staples along said anvil plate toward said anvil surface to locate the forwardmost staple of said row thereon to be formed and implanted thereabout and to be disengaged therefrom when formed and implanted, said surgical staples of said row each having a crown portion terminating at its ends in downwardly depending legs, said surgical staples of said row straddling said raised central portion and said downwardly depending portions of said anvil plate, the free ends of said legs of said surgical staples being supported by said lateral flange portions of said anvil plate, said lateral flange portions having coplanar extensions at said forward end of said anvil plate, said coplanar extensions extending laterally and along said coextensive extension such that the legs of all of said surgical staples of said row, except the forwardmost staple of said row, are supported by said lateral flange portions and said coplanar extensions as said row of staples is urged and advanced along said anvil plate and said coextensive extension by said feeder assembly, said body having a rectilinear inside surface extending upwardly with respect to said anvil surface, a staple driver located within said forward body portion above said anvil surface, said driver being slidable along said rectilinear surface and shiftable therealong longitudinally between a first retracted position and a second extended staple forming and implanting position, a trigger pivotally mounted within said body and rotatable between unactuated and actuated positions, said staple driver having a pair of spaced rearwardly extending tabs thereon, said trigger having a nose portion abutting said stable driver to maintain said staple driver against said inside body surface and being located between said tabs to shift said staple driver between said first and second positions, a rearward portion of said trigger being partially exposed beneath said rearward handle portion of said body for actuation by a surgeon, and means within said body to bias said trigger to said unactuated position and said staple driver to said first position.

2. The structure claimed in claim 1 wherein said means to bias said trigger to said unactuated position and said staple driver to said first position comprises a U-shaped leaf spring located within said body and having a first leg engaging the upper inside surface of said body and a second leg engaging said rearward portion of said trigger.

3. An anvil plate for use with a surgical stapling instrument of the type having a magazine containing a row of staples in face-to-face relationship, each of said staples comprising a crown portion terminating at its ends in downwardly depending legs which in turn terminate in free ends, said anvil plate comprising an elongated member having forward and rearward ends and being of inverted U-shaped cross section, said anvil plate having a longitudinally extending raised central planar portion, the longitudinal edges of which terminate in coextensive downwardly depending portions, each of said downwardly depending portions terminating in a flange portion extending laterally of said downwardly depending portion and said central portion, a coextensive extension on said central portion of said forward end of said anvil plate lying at a slight upward angle to said central portion, said extension comprising an anvil having an upper anvil surface about which said staples are formed, said flange portions extending the length of said anvil plate and having coplanar extensions at the forward end thereof, said coplanar extensions extending laterally and along said coextensive extension such that when said staples of said row are mounted on said anvil plate straddling said raised central portion and said anvil, the free ends of all but the forwardmost staple of said row are supported by said flanges and said coplanar extensions.

* * * * *